US008063376B2

(12) United States Patent
Maniawski et al.

(10) Patent No.: US 8,063,376 B2
(45) Date of Patent: Nov. 22, 2011

(54) LARGE BORE PET AND HYBRID PET/CT SCANNERS AND RADIATION THERAPY PLANNING USING SAME

(75) Inventors: Piotr J. Maniawski, Chagrin Falls, OH (US); Daniel Gagnon, Twinsburg, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 255 days.

(21) Appl. No.: 12/535,722

(22) Filed: Aug. 5, 2009

(65) Prior Publication Data

US 2010/0040197 A1 Feb. 18, 2010

Related U.S. Application Data

(60) Provisional application No. 61/089,193, filed on Aug. 15, 2008.

(51) Int. Cl.
*G01T 1/161* (2006.01)

(52) U.S. Cl. ................................................ 250/363.02

(58) Field of Classification Search ............. 250/363.02
See application file for complete search history.

(56) References Cited

U.S. PATENT DOCUMENTS

| | | | |
|---|---|---|---|
| 4,559,597 A | 12/1985 | Mullani | |
| 7,132,664 B1 * | 11/2006 | Crosetto | 250/367 |
| 7,609,808 B2 * | 10/2009 | Tornai et al. | 378/63 |
| 2007/0080293 A1 * | 4/2007 | Huber et al. | 250/363.02 |

OTHER PUBLICATIONS

Worstell et al., "Design and Performance of prototype Whole Body PET/CT scanner with Fiber optic readout," Oct. 2004, IEEE Nuclear Science Symposium Conference Record, pp. 3280-3284.*
http://www.radiologytoday.net/archive/rt08142006p20.shtml, "Time of Flight—Next-Generation PET Takes Flight", by Dan Harvey, Radiology Today, vol. 7, No. 16 p. 20, 3 pgs., accessed Jul. 9, 2008.
"The Use of PET for Radiotherapy," Yusuf Emre Erdi, Current Medical Imaging Reviews, 2007, 3, pp. 3-16.
"Innovations in Computed Tomography Offer Faster Diagnosis and Treatment of Cancer," report by Philips Medical Systems, Business Briefing: European Oncology Review 2005, pp. 1-3.
http://medgadget.com/archives/2008/06/philips_gemini_tf_big_bore_pet..., "Philips GEMINI TF Big Bore PET/CT Tomograph" 3 pgs., accessed Jul. 8, 2008.

* cited by examiner

*Primary Examiner* — David Porta
*Assistant Examiner* — Christine Sung

(57) ABSTRACT

An imaging system comprises: a ring of positron emission tomography (PET) detectors; a PET housing at least partially surrounding the ring of PET detectors and defining a patient aperture of at least 80 cm; a coincidence detection processor or circuitry configured to identify substantially simultaneous 511 keV radiation detection events corresponding to electron-positron annihilation events; and a PET reconstruction processor configured to reconstruct into a PET image the identified substantially simultaneous 511 keV radiation detection events based on lines of response defined by the substantially simultaneous 511 keV radiation detection events. Radiation planning utilizing such an imaging system comprises: acquiring PET imaging data for a human subject arranged in a radiation therapy position requiring a patient aperture of at least about 80 cm; reconstructing said imaging data into a PET image encompassing an anatomical region to undergo radiation therapy; and generating a radiation therapy plan based on at least the PET image.

32 Claims, 4 Drawing Sheets

LARGE BORE PET AND HYBRID PET/CT SCANNERS AND RADIATION THERAPY PLANNING USING SAME

CROSS REFERENCE TO RELATED APPLICATIONS

This application claims the benefit of U.S. provisional application Ser. No. 61/089,193 filed Aug. 15, 2008, which is incorporated herein by reference.

BACKGROUND

The following relates to the oncological arts, medical imaging arts, positron emission tomography (PET) arts, and related arts.

Radiation therapy has been shown to be effective in treating certain types of cancer. In these techniques, a high dosage of ionizing radiation is applied to the tumor or other malignant tissue. The typically high tissue growth rate and "unnatural" nature of the malignant tissue results in the ionizing radiation preferentially damaging or killing the malignant tissue; however, healthy tissue is also adversely impacted by the ionizing radiation. Accordingly, the ionizing radiation is applied in a tomographic or multi-beam configuration with the beam intensities and, optionally, cross-sectional beam profiles designed to deliver a therapeutic radiation dosage to the target tumor while keeping the radiation dosage received by neighboring critical organs below a design threshold.

Because anatomy varies amongst individuals, radiation therapy is planned on an individual basis for each patient. Anatomical data for the radiation therapy planning is acquired using computed tomography (CT) imaging which measures transmission of a tomographically rotating x-ray beam to enable reconstruction of a three-dimensional image of the internal patient anatomy. CT imaging has numerous advantages for this application—data acquisition is fast (of order a few minutes); it typically provides detailed structural information about both the target tumor and the surrounding critical organs; the x-rays mimic the transmission and absorption characteristics of the therapeutic radiation such that a therapeutic radiation absorption map can be constructed from the CT image using suitable tissue absorption correction factors; and CT scanners can be constructed with large bores.

A typical radiation therapy system has a patient aperture of order 80 centimeters. For example, some commercially available linear accelerator (linac)-based radiation therapy systems have patient apertures of 85 centimeters. Problematically, internal organ positions can shift, rotate, compress, expand, or otherwise differ depending upon the precise patient position. As a result, if the patient has to assume a different position in the CT scanner than in the radiation therapy system due to a smaller patient aperture of the former, then the anatomical images used for therapy planning may not accurately replicate the anatomical configuration during therapy.

By providing a CT scanner with a bore at least as large as that of the radiation therapy system, the patient can be positioned in the CT scanner in the same way the patient is positioned in the radiation therapy system. For example, the patient can have his or her arm or arms elevated or otherwise positioned in such a way as to not impede the therapeutic radiation beam; and, the patient can be positioned in precisely this same way in the large-bore CT scanner. This helps to ensure that organ positions are the same in both the planning CT images and in the radiation therapy system. One CT scanner that has a large bore suitable for radiation therapy planning is the Brilliance™ CT Big Bore™ system (available from Koninklijke Philips Electronics N.V., Eindhoven, the Netherlands), which has a patient aperture of 85 cm.

CT has been, and is expected to remain, a primary tool for acquiring patient anatomical data for planning. However, other imaging modalities could also be useful for radiation therapy planning.

Positron emission tomography (PET) imaging is a good candidate as a secondary imaging modality, because PET provides functional information that is complementary to the structural information provided by CT. In PET imaging, a radiopharmaceutical that emits positrons is administered to the patient. Each emitted positron interacts with a nearby electron in an electron-positron annihilation event that emits two oppositely directed 511 keV gamma rays. These gamma rays are detected substantially simultaneously by a radiation detector ring, thus defining a line-of-response along which the electron-positron annihilation event must (neglecting scattering) have occurred. In "time-of-flight" PET, the slight time difference (or lack thereof) between the two substantially simultaneous gamma ray detection events is used to further localize the annihilation event along the line of response.

The information provided by PET depends upon the radiopharmaceutical and its interaction with the patient physiology. A radiopharmaceutical injected into the bloodstream can inform about blood flow or blood perfusion. Since cancerous tumors tend to have dense vasculature, they are strongly visible in PET images that employ a blood-borne radiopharmaceutical. Similarly, radiopharmaceuticals including glucose cluster in areas of high metabolic activity, such as a cancerous tumor. On the other hand, if the tumor tissue is necrotic (perhaps due to success of previous radiation therapy sessions) then the tumor may be visible in CT images (since it remains structurally intact) but not in PET images (since it is necrotic and is no longer being actively fed by blood flow in the vasculature or metabolizing glucose).

A substantial obstacle to utilizing PET in radiation therapy planning and therapy monitoring is that PET scanners do not have the requisite combination of large patient aperture and high sensitivity. The radiopharmaceutical dosage is strictly limited due to safety concerns. As a result, a PET imaging session can take of order 30 minutes or longer to acquire sufficient data for reconstructing an image useful for oncology. The imaged volume increases with the square of the scanner diameter, which complicates scaling up the geometry to larger size (for example, to an 85 cm patient aperture). Stabilization of the patient in the PET scanner is another issue, especially in some hybrid CT/PET scanners in which the patient is supported by cantilevering in the PET gantry.

A blood borne radiopharmaceutical accumulates in areas of high blood concentration. These areas include the cancerous tumor due to its dense vasculature, but also include the brain and the bladder (the latter being the organ by which the radiopharmaceutical is ultimately excised from the body). The brain and bladder are therefore substantial sources of stray radiation that can lead to false gamma ray counts that degrade image quality. Use of energy-range and time-range filtering reduces these stray counts; however, in human-sized PET scanners these post-acquisition filtering techniques have been found to be insufficient, by themselves, to obtain clinical quality images for oncological applications.

With reference to FIG. 1, therefore, in existing human-sized PET scanners radiation shield rings are included to physically block this stray radiation from reaching the radiation detector ring. FIG. 1 diagrammatically depicts the detector ring 10 in cross-section so as to show the radiation detectors comprising (in this embodiment) a scintillator 12 viewed by photomultiplier tube (PMT) detectors 14. A patient S is arranged with a tumor or other malignancy of interest positioned at an isocenter 16 of the detector ring 10. Side shield rings 20 made of lead or another material with high radiation stopping power extend radially inwardly from the ring of PET detectors so as to block a substantial portion of stray radiation from the brain region B and bladder or kidney region K from reaching the scintillator ring 12. To further illustrate with some typical dimensions, in one commercial PET scanner (the Gemini™ Time-of-Flight PET/CT scanner, available from Koninklijke Philips Electronics N.V., Eindhoven, the Netherlands), the scintillator ring 12 has a diameter of 89 cm, and the shield rings 20 extend radially about 10 centimeters inward, so that the shield rings 20 have an inner diameter of 70 cm. As a result, an exterior housing 22 can have a patient aperture of no larger than about 70 cm, that is, no more than about 79% of the detector ring diameter. A patient aperture of 70 cm is large enough to receive a human subject, but is too small for performing imaging of a human subject in the same position as the subject would assume in the radiation therapy system. For example, the patient could not assume the conventional "frogleg" position used in radiation therapy of the colorectal region.

It has long been believed in the PET imaging arts that side shielding (such as the side shield rings 20) are essential for obtaining oncological quality images. (As used herein, the term "oncological quality images" and the like encompasses images of high resolution and low noise that are suitable for medically acceptable analysis of cancerous tumors and other malignancies for patient health-critical purposes such as radiation therapy planning or other interventional therapy planning or planning decision-making.) For example, Mullani, U.S. Pat. No. 4,559,597 issued in 1985 discloses time-of-flight PET and considers the possibility of operating without side shields (called "septa" in Mullani), but concludes that omitting side shields introduces a substantial amount of scatter in the data and may not be acceptable for a clinically usable system. Mullani concludes that septa of length 12 cm provides optimal performance. Commercial oncology-quality PET scanners today continue to use side shielding of order 10 cm.

Other issues with oncological PET relate to scan time and patient inconvenience. In contrast to CT acquisition which is of order a few minutes, an oncological-quality PET scan can take 30 minutes or longer. Both faster acquisition and improved fusion of CT and PET images could be achieved by using a hybrid PET/CT scanner, in which the CT and PET gantries are arranged coaxially together to receive a subject via a common subject support system. Hybrid PET/CT scanners are available, as exemplified by the aforementioned Gemini™ PET/CT scanner. In most cases, CT is the "primary" imaging modality used in these systems, and hence is positioned closest to the patient loading end. When PET imaging is to be performed, the subject is transferred through the CT gantry and thence into the PET gantry.

However, this arrangement results in cantilevered support of the patient in the PET scanner, with the possible consequence of downward deflection of the patient support and resultant PET/CT image misalignment. Such misalignment can be corrected mathematically during the post-acquisition PET/CT image fusion processing. However, the correction increases computational complexity, and introduces yet another potential source of error in fusing CT and PET images for radiation therapy planning.

The cumulative effect of these issues has led to continued dominance of CT as the radiation therapy planning modality of choice, with PET imaging relegated to an infrequently used secondary planning modality. For example, a recent survey indicates that close to 90% of radiation therapy planning acquisitions employed CT imaging, while less than 10% of those acquisitions also employed PET imaging as a secondary modality. See IMV 2006 Radiation Oncology Census Market Summary Report, March 2007.

The following provides a new and improved apparatuses and methods which overcome the above-referenced problems and others.

BRIEF DESCRIPTION

In accordance with one disclosed aspect, an imaging system for imaging a human subject is disclosed, the imaging system comprising: a ring of positron emission tomography (PET) detectors; a PET housing at least partially surrounding the ring of PET detectors and defining a patient aperture of at least 80 cm; and a coincidence detection processor or circuitry configured to identify substantially simultaneous 511 keV radiation detection events corresponding to electron-positron annihilation events.

In accordance with another disclosed aspect, a method is disclosed, the method comprising: acquiring positron emission tomography (PET) imaging data for a human subject arranged in a radiation therapy position requiring a patient aperture of at least about 80 cm; reconstructing the PET imaging data into a PET image of the human subject which PET image encompasses an anatomical region to undergo radiation therapy with the human subject arranged in the radiation therapy position; and generating a radiation therapy plan based on at least the PET image.

In accordance with another disclosed aspect, an imaging system is disclosed for imaging a human subject, the imaging system comprising: a ring of positron emission tomography (PET) detectors defining a detector ring diameter; a PET housing at least partially surrounding the ring of PET detectors and defining a patient aperture that is smaller than and at least about 85% of the detector ring diameter; and a coincidence detection processor or circuitry configured to identify substantially simultaneous 511 keV radiation detection events corresponding to electron-positron annihilation events.

In accordance with another disclosed aspect, a system is disclosed comprising: a positron emission tomography (PET) imager including a ring of positron emission tomography (PET) detectors and a PET housing at least partially surrounding the ring of PET detectors and defining a PET patient aperture; wherein the PET patient aperture is at least as large as a patient aperture of a radiation therapy system configured to perform radiation therapy on a human subject in a radiation therapy position in accordance with a radiation therapy plan for the human subject generated based at least in part on PET images of the human subject acquired using the PET imager with the human subject in the radiation therapy position.

In accordance with another disclosed aspect, a patient support is disclosed, comprising: a subject table selectively horizontally translatable into a first medical system and into a second medical system; a plurality of spaced apart catchers arranged to support the subject table in the first medical system and in the second medical system; a height synchronization processor operatively coupled with the catchers to maintain a constant height of the subject table both in the first medical system and in the second medical system in the presence of a patient load; and a loading structure at which a subject is loaded onto the subject table.

In accordance with another disclosed aspect, an imaging system is disclosed for imaging a human subject, the imaging system comprising a ring of positron emission tomography (PET) detectors having no side shielding or side shielding of reduced radially inward extent. The ring of PET detectors has a fast response speed effective to enable a narrow coincidence time window for identifying substantially coincident 511 keV detection events, which narrow coincidence time window compensates for additional noise introduced by the lack of side shielding or by the side shielding of reduced radially inward extent.

DETAILED DESCRIPTION

Figure 1:
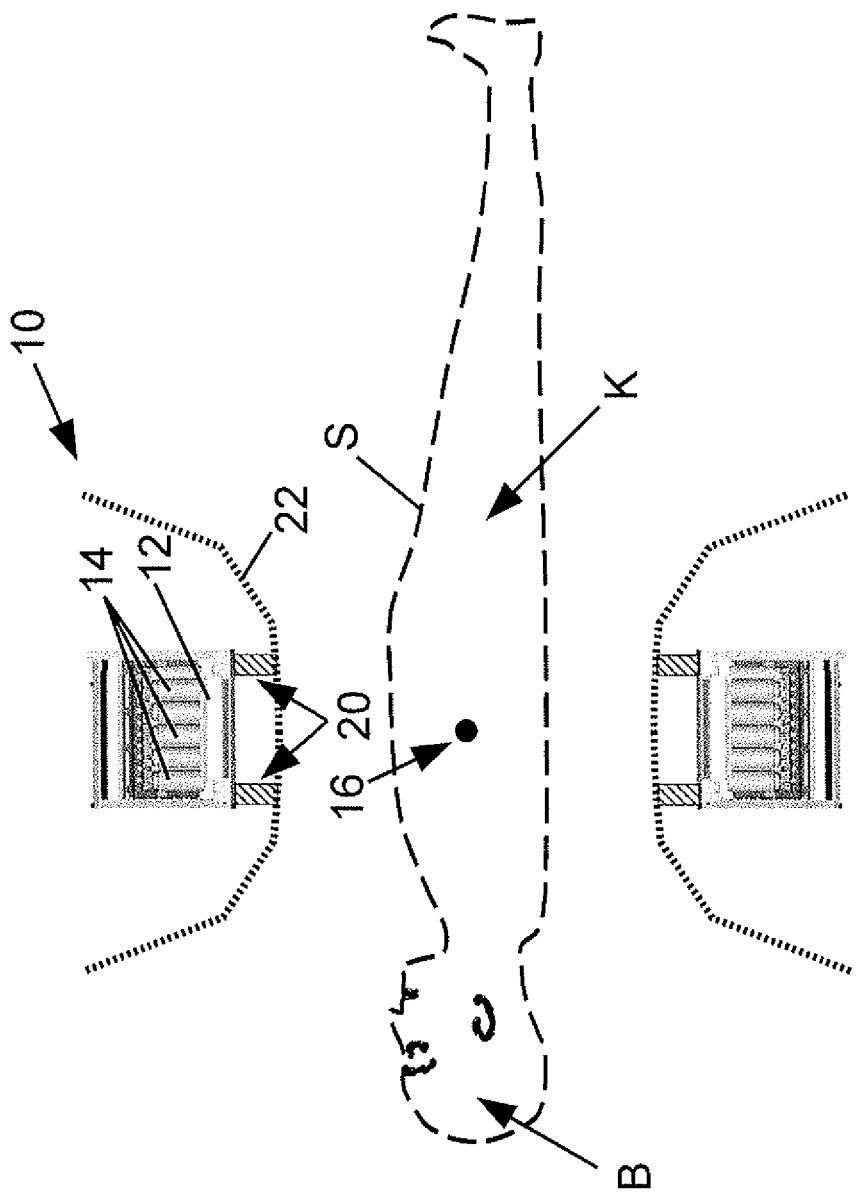
FIG. 1 diagrammatically shows a human-sized PET imaging system in accordance with the prior art, including side shielding to reduce stray radiation detection events.
Figure 2:
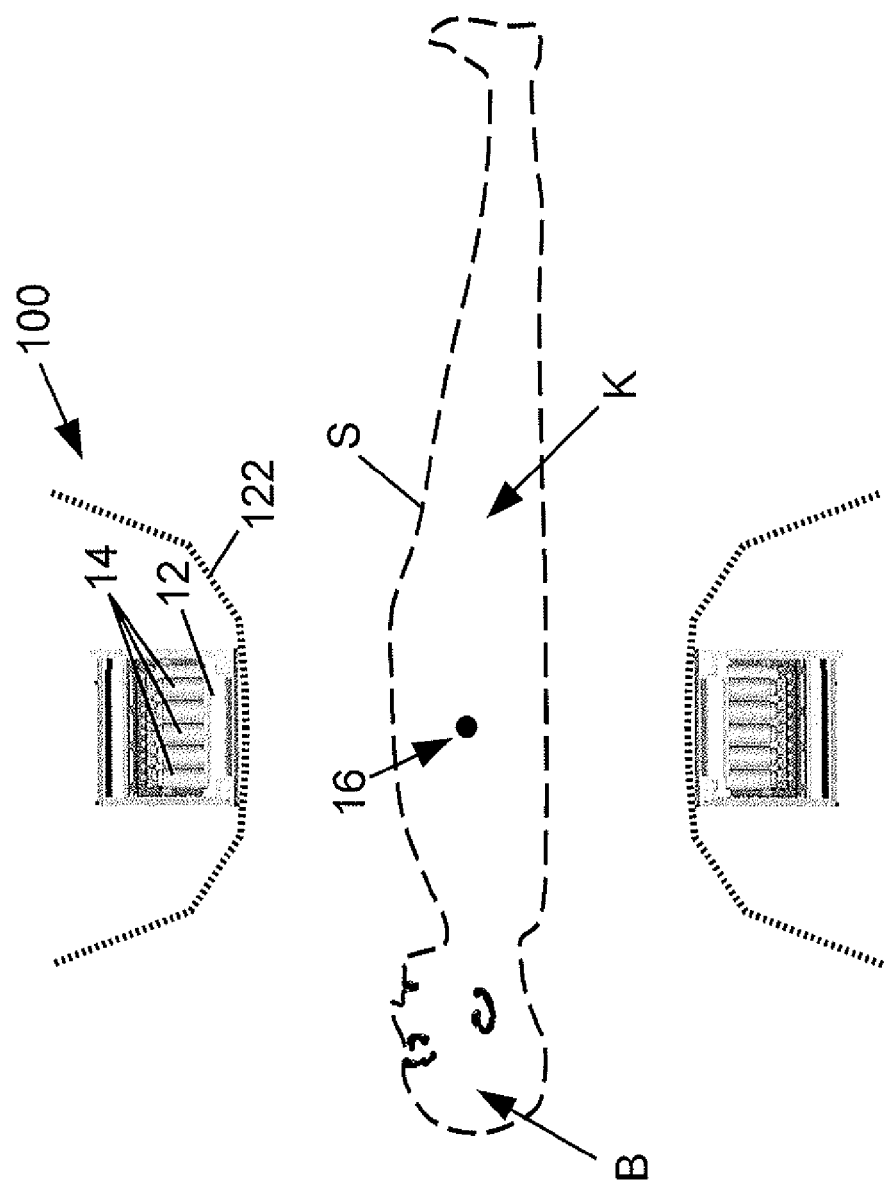
FIG. 2 diagrammatically shows a human-sized PET imaging system with a larger patient aperture than the prior art system of FIG. 1.

With reference to FIG. 2, a detector ring 100 is similar to the detector ring 10 of FIG. 1. The detector ring 100 includes the scintillator ring 12 viewed by photomultiplier tube (PMT) detectors 14. The patient S is arranged with a tumor or other malignancy of interest positioned at the isocenter 16 of the detector ring 100. However, the detector ring 100 omits the side shield rings 20 of the PET scanner of FIG. 1. As a result, a modified PET housing 122 has a larger patient aperture than the housing 22 of the conventional detector ring 10 of FIG. 1. For example, the scintillator ring 12 of the Gemini™ Time-of-Flight PET/CT scanner (available from Koninklijke Philips Electronics N.V., Eindhoven, the Netherlands) has a detector diameter of 89 cm defined by the scintillator ring 12. However, in the Gemini™ PET scanner, the shield rings 20 extend radially about 10 centimeters inward, so that the shield rings 20 have an inner diameter of 70 cm. As a result, the exterior housing 22 of the conventional PET detector ring 10 can have a patient aperture no larger than about 70 cm, that is, about 79% of the detector ring diameter.

In contrast, the detector ring 100 of FIG. 2 has no side shield rings 20, and accordingly is limited in patient aperture only by the scintillator ring 12. If the dimensions of the Gemini™ Time-of-Flight PET/CT scanner are used for this component, then the detector ring 100 in some embodiments has a detector ring diameter of 89 cm. In some actually constructed embodiments, the housing 122 has a patient aperture of 85 cm (allowing for some physical thickness of the housing 122) which comports with the patient aperture for some commercial radiation therapy systems, such as some commercial linac systems. This patient aperture of 85 cm is greater than 95% of the detector ring diameter (89 cm). More generally, it is desired to have the patient aperture be at least 80 cm, and in some more limited embodiments the patient aperature is at least about 85 cm to comport with a conventional linac patient aperture. In terms of percentages, the patient aperture should be at least 85% of the detector ring diameter, and in some embodiments the patient aperture is at least about 90% of the detector ring diameter, and in some further limited embodiments the patient aperture is at least about 95% of the detector ring diameter.

Using the illustrative example of the Gemini™ geometry with its PET detector ring diameter of 89 cm, a target patient aperture of 85% of this illustrative detector ring diameter is about 76 cm. For such an embodiment, it is contemplated to not wholly omit the side shielding rings 20 (as illustrated in FIG. 2), but rather to employ side shielding rings with a reduced inward radial extent. For example, again allowing for some physical thickness of the PET housing 122, to achieve a patient aperture of about 76 cm one can include side shielding rings having an inward radial extent of about 3 cm or less. More generally, one can include side shielding rings extending radially inward from the ring of PET detectors a distance of between zero and no more than about three centimeters. In the embodiment illustrated in FIG. 2, the side shielding rings extend radially inward from the ring of PET detectors a distance of zero centimeters or, in other words, the side shielding rings are omitted entirely. In some embodiments, factors including: cost of the side shielding rings (even with reduced inward radial extent); reduced effectiveness of the side shielding rings with reduced inward radial extent as compared with the larger side shielding rings 20 of a conventional PET scanner; and the possibility of a non-uniform noise distribution across the radiation detectors due to partial but incomplete side shielding; makes it generally preferable to omit the side shielding rings entirely.

The skilled artisan would generally expect that the detector ring 100 diagrammatically depicted in FIG. 2 would be unusable for radiation therapy planning. The skilled artisan would recognize that energy and time windowing can be used to mathematically remove or filter some of this stray radiation, but would nonetheless generally expect that stray radiation from the brain and bladder or kidney regions B, K, or from other sources outside the PET bore, would produce sufficient noise so as to degrade the PET image quality below that acceptable for radiation therapy planning applications. Indeed, to the inventors' knowledge all commercial human-sized PET systems (e.g., with patient aperture of about 70 cm or larger) heretofore have required side radiation shielding 22 having an inward radial extent of order 10 centimeters, as shown in prior art FIG. 1, in order to physically filter out (that is, physically block) much of the stray radiation from the brain and outer regions B, K or from elsewhere outside of the PET bore, so as to achieve PET image quality sufficient for clinical applications such as radiation therapy planning.

Figure 3:
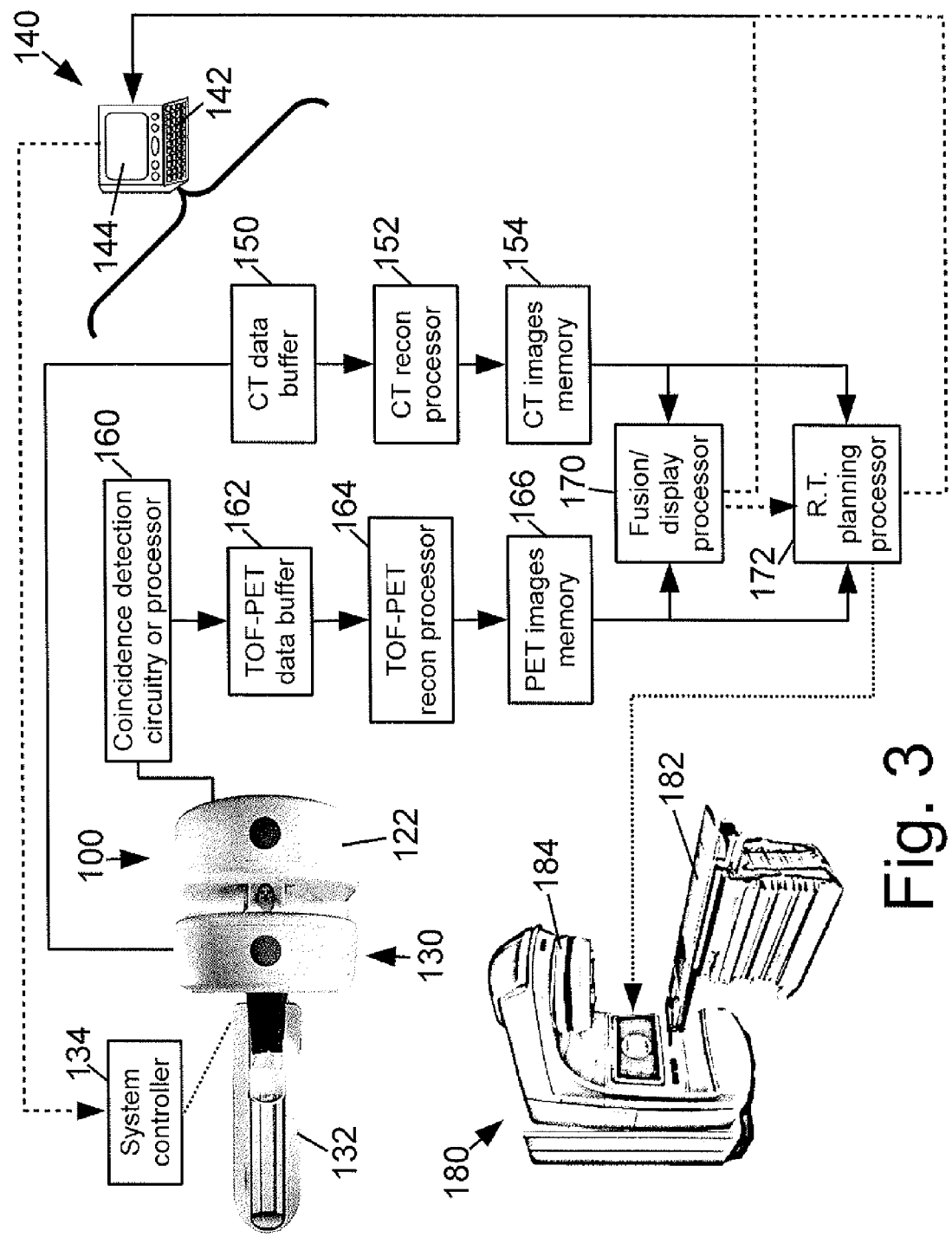
FIG. 3 diagrammatically shows a radiation therapy system including a large-bore CT/PET scanner used for radiation therapy planning including monitoring of radiation therapy treatment progress.

With continuing reference to FIG. 2 and with further reference to FIG. 3, it is however recognized herein that the increased noise due to stray radiation from the outer regions B, K or from elsewhere outside of the PET bore can in practice be compensated by noise reduction achieved using radiation detectors of sufficiently high temporal and energy resolution. In other words, while heretofore it has been believed in the art that side shields (and consequent constriction of the patient aperture) are required to obtain ecological quality images, it is recognized herein that one can omit the side shielding rings 20 and achieve noise reduction by using high-speed radiation detectors to enable narrow time- and energy-windowing during coincidence detection. Suitably high-speed radiation detectors can be constructed using scintillator crystals of materials such as LYSO, LSO, LFS, MLS, LaBr, LuI, LuAG, LuAP, or LGSO crystals, which exhibit rapid scintillation decay times of order a few tens of nanoseconds or shorter. Further, by using high speed detectors one can optionally implement a time-of-flight PET image data reconstruction technique, which provides still further noise reduction.

FIG. 3 depicts (in an overhead view) a hybrid CT/PET scanner including a PET scanner with the detector ring 100 omitting the side shielding rings and accordingly including the PET housing 122 with large patient aperture (e.g., at least 80 cm, and more preferably at least about 85 cm). The PET detector ring 100 is in some embodiments substantively similar to the PET scanner portion of the Gemini™ Time-of-Flight PET/CT scanner (available from Koninklijke Philips Electronics N.V., Eindhoven, the Netherlands) which includes the scintillator ring 12 constructed of 4×4×22 mm lutetiumyttrium oxyorthosilicate (LYSO) crystals defining a detector ring diameter and viewed by the illustrated PMT detectors 14 positioned at a larger diameter than the scintillator ring 12 and defining an Anger-logic detector configuration. LYSO crystals advantageously have sufficiently rapid scintillation decay to provide sub-nanosecond temporal resolution enabling time-of-flight localization of the electron-hole annihilation event along the line-of-response. LYSO crystals are used in the current Gemini™ system, but other scintillators having fast scintillation decay are also contemplated, such as LSO, LaBr, or other crystals. In yet other contemplated embodiments, the PMT detectors 14 are contemplated to be replaced by silicon photomultiplier (SiPM) devices, semiconductor photodetectors, or the like. In still yet other contemplated embodiments, it is contemplated to replace the scintillator ring/photodetector assembly by a ring of direct radiation detectors, such as semiconductor photodetectors configured to directly detect 511 keV radiation without an intermediate scintillation event.

In some embodiments, the PET scanner may be provided alone. However, for radiation therapy planning applications, it is anticipated that CT will likely remain the primary planning mode of choice among many oncologists. Accordingly, the embodiment illustrated in FIG. 3 employs a hybrid CT/PET scanner (shown in overhead view in FIG. 3) that includes, in addition to the PET detector ring 100, a CT scanner 130 having a bore arranged coaxially with the bore of the PET detector ring 100, and further including a common patient support with a patient couch or loading structure 132 configured to load a patent into either the CT scanner 130 (as illustrated) or into the PET detector ring 100. To facilitate imaging of a human subject arranged in a radiation therapy position, the CT scanner 130 has a patient aperture of at least about 80 cm, and more preferably at least about 85 cm. In some embodiments, the PET detector ring 100 and the CT scanner 130 both have the same patient aperture size, so that it is ensured that a human subject arranged in a radiation therapy position that fits into one of the scanners 100, 130 will also fit into the other of the scanners. A system controller 134 provides control interfacing between the hybrid CT/PET scanner and a suitable user interface such as a diagrammatically illustrated computer 140 including one or more user input devices such as an illustrated keyboard 142, a mouse or other pointing device, or so forth, and one or more user output devices such as an illustrated display 144, a printer or other marking engine, or an Internet or local area network (LAN or wireless LAN) interface, or so forth.

The CT scanner 130 is in some embodiments substantively similar to the Brilliance™ CT Big Bore™ system (available from Koninklijke Philips Electronics N.V., Eindhoven, the Netherlands), which has a patient aperture of 85 cm, a 60-70 cm field of view, and employs a 60 kW generator coupled with an x-ray tube drivable at 20-500 mA tube current with a dynamic focal spot. However, other CT scanners having a sufficiently large patient aperture are also contemplated for use as the CT scanner component 130 of the hybrid CT/PET scanner.

With reference to FIG. 3, CT data are acquired by the CT scanner 130 and collected and stored or buffered in a CT data buffer 150, and are reconstructed by a CT reconstruction processor 152 to generate CT images that are stored in a CT images memory 154. The CT reconstruction processor 152 can employ any reconstruction algorithm suitable for reconstructing CT projection data, such as a filtered backprojection algorithm, an iterative reconstruction technique, or so forth.

Processing of data collected by the PET detector ring 100 entails processing by a coincidence detection processor or circuitry 160 that identifies substantially coincident 511 keV gamma ray detection events that are likely to correspond to electron-hole annihilation events. The coincidence detection processor or circuitry 160 preferably performs energy windowing on the individual radiation particle detection events to filter out radiation detection events corresponding to particles (the term "particle" being used broadly herein to encompass both photons and conventional particles such as electrons and protons) having energies substantially different from 511 keV. The coincidence detection processor or circuitry 160 preferably also performs time windowing on prospective pairs of radiation particle detection events to filter out radiation detection event pairs that are temporally separated by time intervals too large to correspond to electron-hole annihilation events. As used herein, substantially coincident 511 keV gamma ray detection events are "substantially coincident" if they are separated by a time interval less than a time window corresponding to a maximum expected time separation for detection of two oppositely directed 511 keV gamma rays emanating from a single electron-positron annihilation event. For example, if the detector ring has a radius of 89 cm, then a suitable time window may be defined as 89 cm divided by the speed of light ($c=3\times10^{10}$ cm/s for a vacuum), that is, a time window of about 3.0 ns. A narrower time window may be suitable if the region in which electron-positron annihilation events are expected to occur is smaller than the 89 cm radius of the detector ring. A wider time window is also contemplated, for example to accommodate somewhat coarser detector temporal resolution.

The output of the coincidence detection processor or circuitry 160 is a list of 511 keV gamma ray detection event pairs likely to correspond to electron-hole annihilation events, along with time stamp information about the precise times of the two 511 keV gamma ray detection events making up the pair. This information is suitably stored or buffered in a time-of-flight PET (TOF-PET) data buffer 162 in a listmode format or in another format that contains the relevant information including detector locations for the two 511 keV gamma ray detection events making up the pair and temporal information about the two 511 keV gamma ray detection events making up the pair.

Because the side shielding rings 20 are omitted in the PET detector ring 100, relatively higher "false" radiation events are expected to be detected by the detector ring 100 as compared with a side-shielded detector ring such as the detector ring 10 depicted in FIG. 1. However, it is recognized herein that by configuring the coincidence detection circuitry or processor 160 in conjunction with high-speed radiation detectors to provide a sufficiently narrow temporal coincidence window, for example a temporal window of about 10 ns or shorter, and more preferably about 6 ns or shorter, and a sufficiently narrow energy window of about 15% FWHM, and more preferably less than or about 12%, centered on 511 keV, oncological quality images can be obtained in spite of the omission of the side shielding rings 20. A coincidence temporal window of about 10 ns or shorter can be usefully employed in conjunction with a scintillator having scintillation decay times of a few tens of nanoseconds or shorter, operated using Anger logic or other data analysis providing radiation particle detection event resolution of order a few nanoseconds or less. A narrow temporal window for coincidence detection is recognized herein to be highly effective for filtering out radiation from outlying regions such as the brain region B or the kidney or bladder region K because radiation events emanating from these outer regions cannot generate two simultaneous 511 keV particles that are both detected by the detector ring 100. Even if the positron-emitting radiopharmaceutical is present in the outer regions B, K, the oppositely directed 511 keV particles generated by an electron-positron annihilation event in an outer region cannot both be detected by the detector ring 100 because only one of the two 511 keV particles (at most) is directed toward the detector ring 100. Accordingly, a narrow time window of about 10 ns or less, and more preferably about 6 ns or less, coupled with an energy window centered at 511 keV with a FWHM of about 15% or less, and more preferably about 12% or less, is highly effective for filtering out these spurious radiation detection events, and this effective coincidence temporal filtering is recognized herein to eliminate the need for the side shielding rings 20.

A time-of-flight PET (TOF-PET) reconstruction processor 164 reconstructs the listmode or otherwise-formatted TOF-PET data to generate a PET image that is stored in a PET images memory 166. The TOF-PET reconstruction processor 164 can employ any reconstruction algorithm suitable for reconstructing into a PET image the substantially simultaneous 511 keV radiation detection events identified by the coincidence detection processor or circuitry 160. The TOF-PET reconstruction is based on time-of-flight localized lines of response defined by the identified substantially simultaneous 511 keV radiation detection events, and can employ various reconstruction techniques such as filtered backprojection, iterative backprojection, or so forth, modified or adjusted to take into account additional information provided by the time-of-flight localization. Although the illustrated reconstruction processor 164 employs time-of-flight localization which advantageously further reduces noise, it is also contemplated to omit time-of-flight localization from the PET image reconstruction processing, and to rely solely on a narrow coincidence time window enabled by use of fast detectors to provide sufficient noise reduction to compensate for omission of the side shields 20. The use of high speed detectors and the consequent ability to use narrow coincidence time windowing (for example, using a coincidence time window of about 10 ns or less, and more preferably about 6 ns or less) and narrow energy windowing (for example, using an energy window of about 15% FWHM or less, and more preferably about 12% FWHM or less) provides an effective reduction in data noise. This noise reduction, in turn, compensates for the increased noise of the PET detector ring 100 compared with the conventional PET detector ring 10 caused by omission of the side shielding rings 22 in the PET detector ring 100. Accordingly, it is unexpectedly obtained that the PET detector ring 100 which omits the side shielding rings 22, operating in conjunction with a fast detector system employing, for example, fast scintillators 12 made of LYSO, LSO, LaBr, or another crystal type exhibiting fast scintillation decay, can be used to generate oncology-quality images of a human subject arranged in a radiation therapy position requiring a patient aperture of at least about 80 cm, and in some embodiments requiring a patient aperture of at least about 85 cm. Optionally, TOF-PET reconstruction processing is used to further reduce noise. Synergistically, the same high-speed detectors that enable narrow coincidence time windowing also facilitate TOF-PET reconstruction processing by providing temporal resolution sufficient to provide TOF spatial localization.

The large patient aperture of the PET detector ring 100, which is enabled by the unexpected recognition that the side shields 20 can be omitted, enables generation of high quality PET images of a human subject arranged in a radiation therapy position. The optional large-bore CT scanner 130 similarly enables generation of high quality CT images of the human subject arranged in the radiation therapy position. A fusion/display processor 170 suitably fuses or spatially registers the CT and PET images using a non-deformational spatial registration algorithm. The use of a non-deformational spatial registration algorithm is enabled by the ability of both the CT scanner 130 and the PET detector ring 100 to image the subject in the same radiation therapy position. Accordingly, there is no need to deform either the CT image or the PET image in order to achieve spatial registration. Indeed, in some embodiments the fusion/display processor 170 employs a completely rigid spatial registration algorithm for spatially registering or fusing the CT and PET images.

The fused or spatially registered CT and PET images can be formatted by the fusion/display processor 170 for display on the display 144 of the computer 140. Additionally or alternatively, a radiation therapy planning processor 172 can receive the spatially registered or fused CT and PET images and can perform radiation therapy planning using this patient-specific input information. The radiation therapy planning is typically a user-interactive process, in which a radiologist, oncologist, or other suitably trained person delineates the tumor or other malignancy as well as critical organs or other critical anatomy for which radiation exposure is to be limited or constrained. These features are suitably delineated by the trained person using the user interface 140 and a suitable graphical input such as a touchscreen, mouse, or the like to enable the trained person to draw a line around or otherwise delineate the features in different views or planes (e.g., axial, sagittal, and coronal views, or other views comporting with the spatial orientation or shape of the feature being delineated). The radiation therapy planning processor 172 then calculates a radiation therapy plan that is expected to deliver a desired dosage of radiation to the tumor or other malignancy while keeping the dosage delivered to the delineated critical organs to below a specified level or in compliance with other constraint. The radiation therapy planning processor 172 plans the radiation therapy by computing appropriate values for adjustable parameters of the radiation therapy system, such as radiation beam intensity and area profile (controllable, for example, using a multi-leaf collimator to open or shutter selected beamlets of the radiation beam). For a tomographic radiation therapy system, the beam intensity and area profile may be adjusted as a function of angular position of the radiation source (e.g., linac) as the source revolves around the human subject. For a multi-beam radiation therapy system, the different radiation beams are differently adjusted to effectuate the desired dosage distribution.

The radiation therapy plan generated by the radiation therapy planning processor 172 is carried out by a suitable radiation therapy system, such as an illustrated tomographic radiation therapy system 180 (diagrammatically shown in a perspective view in FIG. 3), or a fixed multi-beam radiation therapy system. The illustrative tomographic radiation therapy system 180 includes a patient support 182 so as to support the human subject arranged in the radiation therapy position for exposure to a rotating radiation source 184 in accordance with the radiation therapy plan. Although illustrated as having separate patient supports 132, 182, it is contemplated to have a common patient couch or loading structure used for both the imaging and radiation therapy systems, for example in the form of a "hybrid" linac/PET system. That is, it is contemplated to integrate the radiation therapy system with the PET detector ring 100, and optionally with the CT scanner 130, so that they are coaxially arranged with a single patient support system configured to move the human subject between the different systems. The use of a single support system to coaxially move the patient into the imaging and radiation therapy sub-systems enables the patient to hold or be constrained in a preselected fixed position in all modalities. It becomes unnecessary to attempt to reposition the patient in the same position for the planning imaging data acquisition and radiation therapy phases. In other embodiments, the radiation therapy system 180 and the CT/PET system may be located in different rooms, different buildings, or so forth.

The CT imaging can be used to determine radiation absorption or attenuation characteristics for use in correcting the PET imaging data for absorption, or for use in the radiation therapy planning. Having the patient in the same radiation therapy position during CT imaging, PET imaging, and radiation therapy enables such absorption or attenuation correction to be performed more accurately.

As used herein, the term "radiation therapy planning" and similar terminology is intended to encompass the initial radiation therapy planning as well as any subsequent radiation therapy monitoring, updating, adjusting, or so forth. For example, PET imaging to assess whether radiation therapy sessions performed to date have converted a tumor (or portion thereof) to a necrotic state qualify as radiation therapy planning, as that term is used herein. (Indeed, such assessment PET imaging may alter the radiation therapy, as for example if the tumor is indeed partially or wholly necrotic then scheduled future radiation therapy sessions may be adjusted or canceled altogether). Moreover, the radiation therapy can employ any of various types of therapeutic radiation, such as an electron beam, gamma beam, proton beam, or so forth.

The illustrated computational or processing components 134, 152, 160, 164, 170, 172 can be variously embodied and variously integrated or separated. For example, in one contemplated arrangement the computer 140 including suitable software or programming embodies at least the imaging system controller 134 and the reconstruction processors 152, 164. The coincidence detection processor or circuitry 160 can be embodied by the computer 140, or can be embodied by electronic components disposed on or in the PET detector ring 100. The latter arrangement can be beneficial for ensuring sufficient processing and signal propagation speeds to enable TOF temporal resolution. For example, in some embodiments on-board electronics of the PET detector ring 100 perform analog-to-digital (A/D) conversion of the radiation particle energy and generate a digital timestamp for each radiation particle detection event so that listmode-formatted data of the form (energy, detector location, time) or the like is outputted off the PET detector ring 100. This listmode-formatted data is then analyzed at the computer 140 or another component to perform energy windowing, time windowing, and coincidence detection. In such embodiments, the coincidence detection processor or circuitry 160 is distributed between the PET detector ring 100 and one or more other, "off-gantry" components. Various other combinations or separations or distributions of the various computational or processing components 134, 152, 160, 164, 170, 172 are also contemplated.

It is also to be appreciated that the various computational or processing components 134, 152, 160, 164, 170, 172 can be variously embodied as digital data storage elements that store software or other instructions executable by the computer 140 and/or another digital processor or processors to perform the described processing operations such as windowing, coincidence detection, image reconstruction, scanner control, and so forth. For example, the digital data storage element or elements may include one or more of the following: a magnetic disk; a magnetic tape; an optical disk; a random access memory (RAM); a read-only memory (ROM); a FLASH memory; a remote Internet or LAN server storage medium; or so forth.

Figure 4:
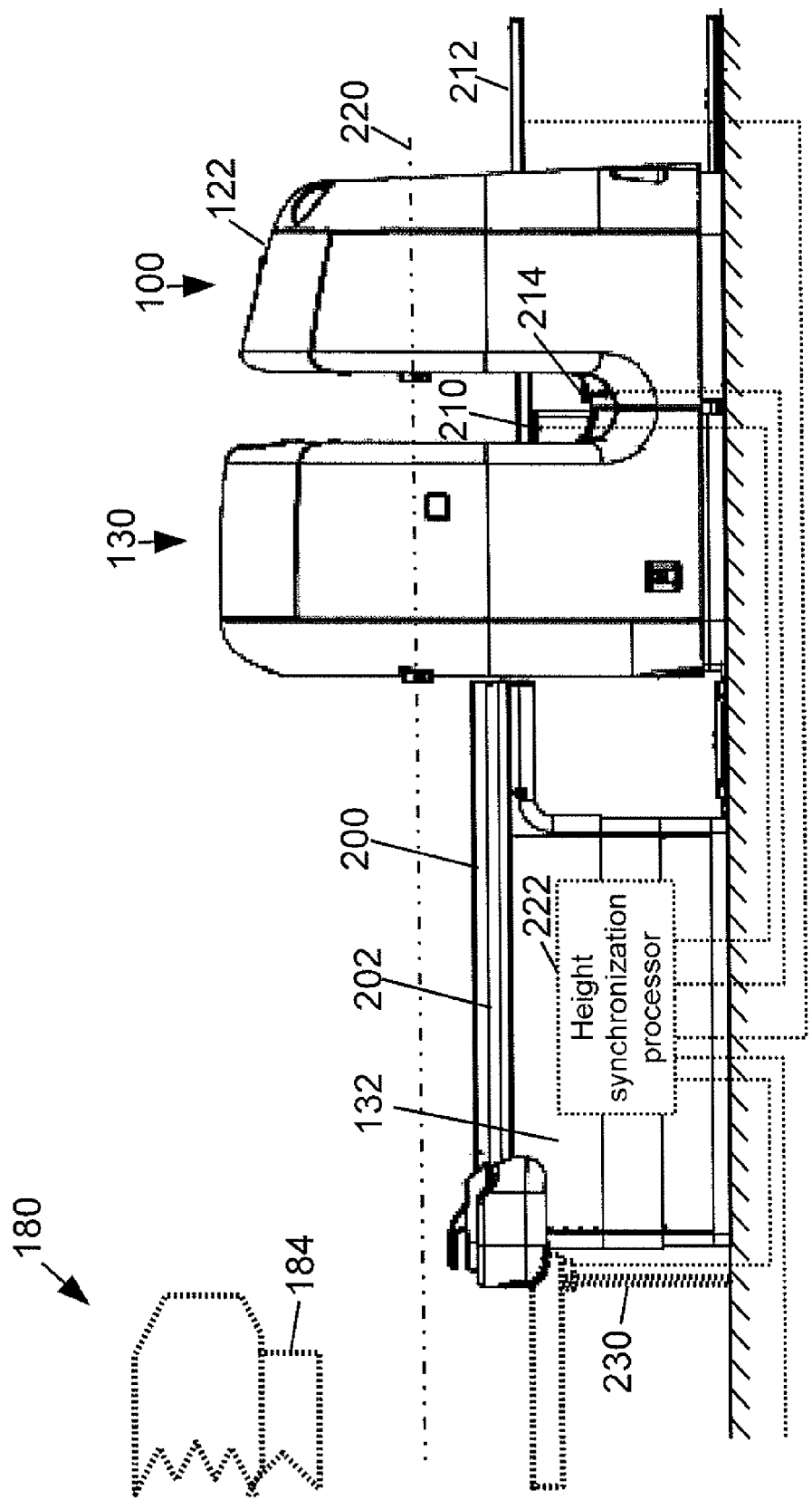
FIG. 4 diagrammatically shows a side view of the CT/PET scanner of FIG. 3, including selected aspects of the patient support system.

With reference to FIG. 4, an illustrative embodiment of the patient support system for the CT/PET scanner including the patient couch or loading structure 132 is described. In the illustrated hybrid scanner embodiment, the CT scanner 130 is assumed to be the "primary" or most commonly used imaging modality, and accordingly is positioned closest to the patient couch or loading structure 132. In this way, if only CT imaging is to be performed, then the human subject need only be moved a relatively short distance into the CT scanner 130. On the other hand, if PET imaging is to be performed, the human subject is moved through the CT scanner 130 and thence into the coaxially aligned patient aperture of the PET detector ring 100. It is also contemplated to arrange the PET and CT scanners in reverse order in the hybrid system, that is, with the PET scanner positioned closest to the patient couch or loading structure 132. In other contemplated embodiments, the patient couch or loading structure 132 may be arranged between the PET and CT scanners. To achieve a two stage subject movement as in the illustrated embodiment (or, alternatively, as in a PET/CT scanner in which the patient couch or loading structure is proximate to the PET scanner and not between the PET and CT scanners), the illustrated patient support system includes a top table or pallet 200 and a bottom table or pallet 202. The two tables or pallets 200, 202 are aligned together (as illustrated in FIG. 4) when the human subject is loaded at the patient couch or loading structure 132, and move together to position the human subject in the CT scanner 130. If it is desired to move the human subject further, into the PET detector ring 100 for PET imaging, then the bottom table or pallet 202 locks into position in the CT scanner using a suitable locking mechanism (not shown) that is activated by sufficient travel of the combined pallets 200, 202 into the CT scanner. Once the bottom pallet 202 locks into position responsive to sufficient forward travel, the top pallet 200 continues to move by itself (that is, moves relative to the stationary locked bottom pallet 202) to transfer the subject into the PET detector ring 100. The reverse process is performed to return the human subject back together with the pallets 200, 202 onto the patient couch or loading structure 132 for convenient unloading.

In some embodiments, one or both pallets may be supported in a cantilevered position when extended into the imaging systems 100, 130. Such an arrangement can lead to downward deflection of the cantilevering end of the pallet, which can cause misregistration of the CT and PET images. Such misregistration is suitably corrected by the fusion/display processor 170.

In the illustrated embodiment, the pallets 200, 202 are not cantilevered, but rather are supported by additional spaced-apart catchers of the patient support system. A CT catcher 210 is arranged to catch or support the end of the bottom pallet 202 distal from the patient couch or loading structure 132 when the pallets 200, 202 are extended into the CT scanner 130. A PET catcher 212 is arranged to catch or support the end of the top pallet 200 distal from the patient couch or loading structure 132 when the top pallet 200 is further extended into the PET detector ring 100. Additional catchers, such as an illustrated intermediate "open position" catcher 214 (shown in a retracted "non-use" position in FIG. 4) can be included to provide further support for one or both pallets 200, 202.

The patient couch or loading structure 132 and the catchers 210, 212, 214 (the latter when extended into the operational position) each have a height that is adjusted to maintain a level of the pallets 200, 202 respective to a suitable reference, such as a central axis 220 of the coaxially aligned CT and PET patient apertures, or respective to another reference. In some embodiments, these heights are adjusted manually in an initial patient support system alignment process. For example, the alignment can utilize a phantom (not shown) having a defined height reference point mounted on the top pallet 200, and alignment lasers are suitably used to ensure that the height reference point of the phantom remains at the designated height as it is moved into the CT scanner 130 and thence into the PET detector ring 100. However, this approach may be insufficient to maintain the subject table 200, 202 at a constant height effective to comply with the Task Group 66 (TG-66) subject table deflection standard promulgated by the American Association of Physicists in Medicine (AAPM) and utilized in the industry as a standard with which medical imaging subject supports preferably comply. For example, subjects of different weights may produce different amounts of table sag, which is not compensated by the manual table support height alignment process.

In the illustrated embodiment, the catchers 210, 212, 214 each include automatic height adjustment actuator, for example a hydraulic piston, pneumatic piston, or other automatic actuator (not shown), and a height synchronization processor 222 operates the automatic height adjustment actuators of the catchers 210, 212, 214 to maintain the target height for the tables 200, 202, preferably at a precision complying with the TG-66 subject table deflection standard promulgated by the AAPM. The height synchronization processor 222 can operate in various ways. In an open-loop approach, the weight of the human subject about to be imaged is input by the radiologist, oncologist, or other trained operator, or is measured using a weight scale (not shown) built into the patient couch or loading structure 132. The height synchronization processor 222 then adjusts the actuators of the catchers 210, 212, 214 to values obtained from a look-up table, mathematical calibration function, or other source so as to compensate for the input or measured weight of the subject. In a closed-loop approach, sensors (not shown) in the catchers 210, 212, 214 actively measure the heights of the respective catchers 210, 212, 214 as they are loaded down with the pallet or pallets 200, 202 bearing the weight of the human subject to be imaged. The height synchronization processor 222 then adjusts the actuators using a feedback controller or feedback control algorithm to maintain setpoint heights for the catchers 210, 212, 214.

In FIG. 4, the height synchronization processor 222 is diagrammatically illustrated as integrated with the patient couch or loading structure 132. In other embodiments, the height synchronization processor 222 may be embodied as the computer 140 executing suitable software, or as a digital storage medium storing said software, or may be otherwise embodied and/or located. Moreover, if the linac or other radiation therapy system 180 is integrated coaxially with the imaging system using a common patient couch or support system (diagrammatically indicated in phantom and in part in FIG. 4), then additional catchers 230 can be included and height-synchronized as described for the catchers 210, 212, 214 in order to maintain a common calibrated height of the patient in the imaging system 100, 130 and in the radiation therapy system 180. By interposing the subject support 132 between the radiation therapy system 180 and the imaging systems 100, 130, spatial separation therebetween is enhanced so as to reduce a likelihood of detrimental interaction between the radiation therapy system 180 and the imaging systems 100, 130. However, it is also contemplated to place the subject support at one end or extremity of the coaxial arrangement of radiation therapy and imaging systems.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An imaging system for imaging a human subject, the imaging system comprising:
   a ring of positron emission tomography (PET) detectors including scintillators selected from the group consisting of lutetium yttrium oxyorthosilicate (LYSO), lutetium oxyorthosilicate (LSO), and lanthium bromide (LaBr) and optical sensors;
   a PET housing at least partially surrounding the ring of PET detectors and defining a patient aperture of at least 80 cm; and
   a coincidence detection processor or circuitry configured to identify substantially simultaneous 511 keV radiation detection events corresponding to electron positron annihilation events, the coincidence detection processor or circuitry being configured to identify substantially simultaneous 511 keV radiation detection events corresponding to electron positron annihilation events using a narrow energy window of about 15% FWHM or shorter and a narrow time window of about 10 ns or shorter.

2. The imaging system as set forth in claim 1, further comprising:
   a time of flight PET reconstruction processor configured to reconstruct into a PET image the identified substantially simultaneous 511 keV radiation detection events based on time of flight localized lines of response defined by the substantially simultaneous 511 keV radiation detection events.

3. The imaging system as set forth in claim 1, wherein the optical sensors include silicon photomultipliers (SiPMs).

4. The imaging system as set forth in claim 1, wherein the imaging system includes side shielding rings extending radially inward from the ring of PET detectors a distance of between zero and no more than about three centimeters.

5. The imaging system as set forth in claim 4, wherein the side shield rings extend a distance greater than zero.

6. The imaging system as set forth in claim 5, wherein the ring of PET detectors comprise scintillators having scintillation decay times of a few tens of nanoseconds or less.

7. The imaging system as set forth in claim 1, wherein the optical sensors are solid state optical sensors.

8. The imaging system as set forth in claim 1, further comprising:
   a computed tomography (CT) scanner defining a CT patient aperture arranged coaxially with and at least as large as the patient aperture defined by the PET housing surrounding the ring of PET detectors.

9. The imaging system as set forth in claim 8, further including:
a radiation therapy system; and
a patient support system which moves a patient among the PET housing patient aperture, the CT scanner patient aperture, and the radiation therapy system.

10. The imaging system as set forth in claim 8, further comprising:
a patient support system including:
a plurality of spaced apart catchers arranged to support a subject table in (i) a PET imaging position aligned with the patient aperture defined by the PET housing surrounding the ring of PET detectors and (ii) a CT imaging position aligned with the CT patient aperture, and
a height synchronization processor operatively coupled with the catchers to maintain a constant height of the subject table in the presence of a patient load.

11. The imaging system as set forth in claim 10, wherein the catchers have an adjustable height which height is adjusted by the height synchronization processor and wherein the height synchronization processor controls the height of the catchers in accordance with a weight of the patient.

12. A method comprising:
acquiring positron emission tomography (PET) imaging data for a human subject arranged in a radiation therapy position requiring a patient aperture of at least about 80 cm;
processing the PET imaging data with a time window of 10 ns or less and an energy window of 15% FWHM or less to identify coincident PET imaging data for reconstruction;
reconstructing the coincident PET imaging data into a PET image of the human subject which PET image encompasses an anatomical region to undergo radiation therapy with the human subject arranged in the radiation therapy position; and
generating a radiation therapy plan based on at least the PET image.

13. The method as set forth in claim 12, further comprising:
acquiring computed tomography (CT) imaging data from the human subject arranged in the radiation therapy position requiring a patient aperture of at least about 80 cm; and
reconstructing the CT imaging data into a CT image of the human subject which CT image encompasses an anatomical region to undergo radiation therapy with the human subject in the radiation therapy position;
the generating of the radiation therapy plan being based on at least both the PET image and the CT image.

14. The method as set forth in claim 13, further comprising:
supporting the human subject arranged in the radiation therapy position requiring a patient aperture of at least about 80 cm during the acquiring of the PET imaging data using a first one or more of a plurality of height adjustable catchers of a patient support system;
supporting the human subject arranged in the radiation therapy position requiring a patient aperture of at least about 80 cm during the acquiring of the CT imaging data using a second one or more of a plurality of height adjustable catchers of the patient support system; and
synchronous adjusting the height of the first and second catchers based on a weight of the human subject to maintain the human subject at a common height and position during both the acquiring of the PET imaging data and the acquiring of the CT imaging data.

15. The method as set forth in claim 14, further comprising:
supporting the human subject arranged in the radiation therapy position in a radiation therapy apparatus having a patient aperture of at least about 80 cm;
performing radiation therapy in accordance with the radiation therapy plan on the human subject in the radiation therapy apparatus; and
further synchronizing the supporting of the human subject in the radiation therapy apparatus to maintain the human subject at said common height during the performing of radiation therapy.

16. The method as set forth in claim 12, wherein the acquiring is performed with the human subject arranged in the radiation therapy position requiring a patient aperture of at least about 85 cm.

17. The method as set forth in claim 12, wherein the acquiring includes converting radiation into light using a scintillator from the group consisting of LYSO, LSO, LaBr, LuI, LuAP, and LGSO and the acquiring is performed without physically blocking stray radiation using side shielding rings.

18. The method as set forth in claim 12, further comprising:
performing radiation therapy on the anatomical region to undergo radiation therapy (i) with the human subject arranged in the radiation therapy position and (ii) using the radiation therapy plan generated based on at least the PET image.

19. An imaging system for imaging a human subject, the imaging system comprising:
a ring of positron emission tomography (PET) detectors defining a detector ring diameter;
a PET housing at least partially surrounding the ring of PET detectors and defining a PET patient aperture that is smaller than and at least about 85% of the detector ring diameter; and
a coincidence detection processor or circuitry configured to identify substantially simultaneous 511 keV radiation detection events corresponding to electron positron annihilation events, the coincidence detection processor or circuitry is configured to identify substantially simultaneous 511 keV radiation detection events using a narrow coincidence temporal window of about 6 ns or smaller and a narrow coincidence energy window of about 12% FWHM or smaller.

20. The imaging system as set forth in claim 19, further comprising:
a time of flight PET reconstruction processor configured to reconstruct into a PET image the identified substantially simultaneous 511 keV radiation detection events based on time of flight localized lines of response defined by the substantially simultaneous 511 keV radiation detection events.

21. The imaging system as set forth in claim 19, further including:
a second diagnostic scanner housing which houses a second diagnostic scanner and has a second patient aperture arranged coaxially with and at least as large as the patient aperture defined by the PET housing surrounding the ring of PET detectors;
a subject support system including height adjustable catchers which support a patient supporting table in the PET and second patient apertures; and
a synchronization processor which controls the height adjustable catchers, based on feedback from the catchers, to maintain height set points for the catchers.

22. The imaging system as set forth in claim 19, wherein the PET housing defines a patient aperture that is at least about 90% of the detector diameter.

23. The imaging system as set forth in claim 19, further comprising:
- a computed tomography (CT) scanner defining a CT patient aperture arranged coaxially with and at least as large as the patient aperture defined by the PET housing surrounding the ring of PET detectors.

24. The imaging system as set forth in claim 19, wherein the ring of positron emission tomography (PET) detectors comprise:
- a scintillator ring comprising scintillator crystals, the scintillator ring defining the detector diameter; and
- optical detectors arranged at a diameter larger than the detector diameter and viewing the scintillator crystals to detect scintillations generated in the scintillator crystals.

25. The imaging system as set forth in claim 19, wherein the patient aperture defined by the PET housing is at least 80 cm.

26. A system comprising:
- a positron emission tomography (PET) imager including a ring of positron emission tomography (PET) detectors and a PET housing at least partially surrounding the ring of PET detectors and defining a PET patient aperture;
- wherein the PET patient aperture is at least as large as a patient aperture of a radiation therapy system configured to perform radiation therapy on a human subject in a radiation therapy position in accordance with a radiation therapy plan for the human subject generated based at least in part on PET images of the human subject acquired using the PET imager with the human subject in the radiation therapy position;
- a subject support having a horizontally translating pallet, the PET patient aperture being arranged relative to the patient aperture of the radiation therapy system such that the human subject can be disposed on the horizontally translating pallet in the radiation therapy position and horizontally translated into either the PET imager or the radiation therapy system without changing position;
- height adjustable catchers which support the pallet in the PET imager and the radiation therapy system;
- a processor which sets a height set point for the catchers based on the subject's weight and adjusts the catchers using feedback to maintain the height set points.

27. The system as set forth in claim 26, further comprising:
- a computed tomography (CT) imager arranged coaxially respective to the subject support such that the human subject disposed on the horizontally translating pallet in the radiation therapy position can also be horizontally translated into the CT imager without changing position and wherein the height adjustable catchers support the pallet in the CT imager.

28. A patient support comprising:
- a subject table selectively horizontally translatable into a first medical system and into a second medical system;
- a plurality of spaced apart catchers arranged to support the subject table in the first medical system and in the second medical system, the catchers each include an actuator which adjusts a height of the catcher;
- a height synchronization processor operatively coupled with the actuators to maintain a constant height of the subject table both in the first medical system and in the second medical system in the presence of a patient load; and
- a loading structure at which a subject is loaded onto the subject table, the first medical system being disposed between the loading structure and the second medical system.

29. The patient support as set forth in claim 28, wherein the first medical system and the second medical system are each selected from a group consisting of (i) a computed tomography (CT) scanner and (ii) a positron emission tomography (PET) scanner.

30. The patient support as set forth in claim 28, wherein the second medical system defines a subject receiving region in which the table supports the subject on the table and wherein the catchers are disposed on both sides of the subject receiving region and wherein the height synchronization processor controls the actuators of the catcher on at least one side of the second medical system to compensate for table deflection due to a weight of the subject.

31. The patient support as set forth in claim 28, wherein the height synchronization processor controls the actuators to set a height of the table at height set points.

32. The patient support as set forth in claim 31, wherein the height synchronization processor adjusts the actuators based on feedback to maintain the height set points.

* * * * *